(12) United States Patent
Kerr et al.

(10) Patent No.: US 8,409,246 B2
(45) Date of Patent: Apr. 2, 2013

(54) APPARATUS FOR PERFORMING AN ELECTROSURGICAL PROCEDURE

(75) Inventors: Duane E. Kerr, Loveland, CO (US); David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 275 days.

(21) Appl. No.: 12/792,019

(22) Filed: Jun. 2, 2010

(65) Prior Publication Data

US 2011/0301637 A1    Dec. 8, 2011

(51) Int. Cl.
*A61B 17/00* (2006.01)
(52) U.S. Cl. ........................................ 606/206
(58) Field of Classification Search .... 227/175.1–182.1; 606/151, 206
See application file for complete search history.

(56) References Cited

U.S. PATENT DOCUMENTS

| | | | |
|---|---|---|---|
| D263,020 S | 2/1982 | Rau, III | |
| 4,728,020 A * | 3/1988 | Green et al. | 227/19 |
| D295,893 S | 5/1988 | Sharkany et al. | |
| D295,894 S | 5/1988 | Sharkany et al. | |
| 5,250,056 A | 10/1993 | Hasson | |
| D348,930 S | 7/1994 | Olson | |
| 5,403,342 A | 4/1995 | Tovey et al. | |
| 5,454,378 A | 10/1995 | Palmer et al. | |
| 5,643,294 A | 7/1997 | Tovey et al. | |
| D384,413 S | 9/1997 | Zlock et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,743,240 B2 | 6/2004 | Smith et al. | |
| D493,888 S | 8/2004 | Reschke | |
| D496,997 S | 10/2004 | Dycus et al. | |
| D499,181 S | 11/2004 | Dycus et al. | |
| 6,818,007 B1 | 11/2004 | Dampney et al. | |
| D509,297 S | 9/2005 | Wells | |
| D525,361 S | 7/2006 | Hushka | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 12/244,873, filed Oct. 3, 2008.

(Continued)

*Primary Examiner* — Gary Jackson
*Assistant Examiner* — Amy Shipley

(57) ABSTRACT

An endoscopic forceps is provided and includes a housing having a shaft. An end effector assembly operatively connects to a distal end of the shaft and has a pair of first and second jaw members. One of the first and second jaw members is movable relative to the other jaw member from an open position, to a clamping position. One of the first and second jaw members includes one or more cam slots defined therein and configured to receive a cam member that upon movement thereof rotates the movable jaw member from the open position to the clamping position. A resilient member is operably coupled to the jaw member that includes the one or more cam slots. The resilient member is configured to provide a camming force to the cam slot and to bias the first and second jaw members in the clamping position.

13 Claims, 5 Drawing Sheets

U.S. PATENT DOCUMENTS

| | | | |
|---|---|---|---|
| D531,311 S | 10/2006 | Guerra et al. | |
| D533,942 S | 12/2006 | Kerr et al. | |
| D535,027 S | 1/2007 | James et al. | |
| 7,195,631 B2* | 3/2007 | Dumbauld | 606/51 |
| D541,418 S | 4/2007 | Schechter et al. | |
| D541,938 S | 5/2007 | Kerr et al | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,766,910 B2 | 8/2010 | Hixson | |
| 7,918,848 B2 | 4/2011 | Lau | |
| 2003/0114851 A1* | 6/2003 | Truckai et al. | 606/51 |
| 2006/0217697 A1 | 9/2006 | Lau et al. | |
| 2007/0173814 A1 | 7/2007 | Hixson et al. | |
| 2007/0260242 A1 | 11/2007 | Dycus et al. | |
| 2009/0018535 A1* | 1/2009 | Schechter et al. | 606/33 |
| 2009/0209960 A1* | 8/2009 | Chojin | 606/51 |
| 2009/0312773 A1* | 12/2009 | Cabrera et al. | 606/144 |
| 2011/0301600 A1* | 12/2011 | Garrison et al. | 606/46 |
| 2011/0301603 A1* | 12/2011 | Kerr et al. | 606/52 |
| 2011/0301606 A1* | 12/2011 | Kerr | 606/52 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 20121161 | 4/2002 |
| DE | 10045375 | 10/2002 |
| DE | 20 2007 00931 | 10/2007 |
| DE | 19738457 | 1/2009 |
| EP | 0584787 | 3/1994 |
| EP | 1159926 | 12/2001 |
| EP | 1177771 A1 | 2/2002 |
| EP | 1777771 | 2/2002 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |
| WO | WO 2008045348 | 4/2008 |
| WO | WO2008045348 A2 | 4/2008 |
| WO | WO 2009039179 | 3/2009 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2; pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8. dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.

Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report EP11168419.7 dated Aug. 8, 2011.
International Search Report EP11168419.7 dated Oct. 11, 2011.
International Search Report EP11168455.1 dated Sep. 26, 2011.
European Search Report for European Application No: 11168458.5 dated Jul. 21, 2011.
European Search Report for European Application No: 12169753.6 dated Sep. 14, 2012.

* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members providing a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

SUMMARY

The present disclosure provides an endoscopic forceps. The endoscopic forceps includes a housing having a shaft. An end effector assembly operatively connects to a distal end of the shaft and has a pair of first and second jaw members. One of the first and second jaw members is movable relative to the other jaw member from an open position, to a clamping position. One of the first and second jaw members includes one or more cam slots defined therein and configured to receive a cam member that upon movement thereof rotates the movable jaw member from the open position to the clamping position. A resilient member is operably coupled to the jaw member that includes the one or more cam slots. The resilient member is configured to provide a camming force to the cam slot and to bias the first and second jaw members in the clamping position.

The present disclosure provides an end effector adapted for use with a forceps including at least one shaft. The first and second jaw members operably couples to a distal end of the shaft. One or both of the first and second jaw members is movable relative to the other from an open position, to a clamping position. One of the first and second jaw members includes one or more cam slots defined therein and configured to receive a cam member that upon movement thereof rotates the jaw members from the open position to the clamping position. A resilient member is operably coupled to the jaw member that includes the at least one can slot. The resilient member is configured to provide a camming force to the cam slot and to bias the first and second jaw members in the clamping position.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
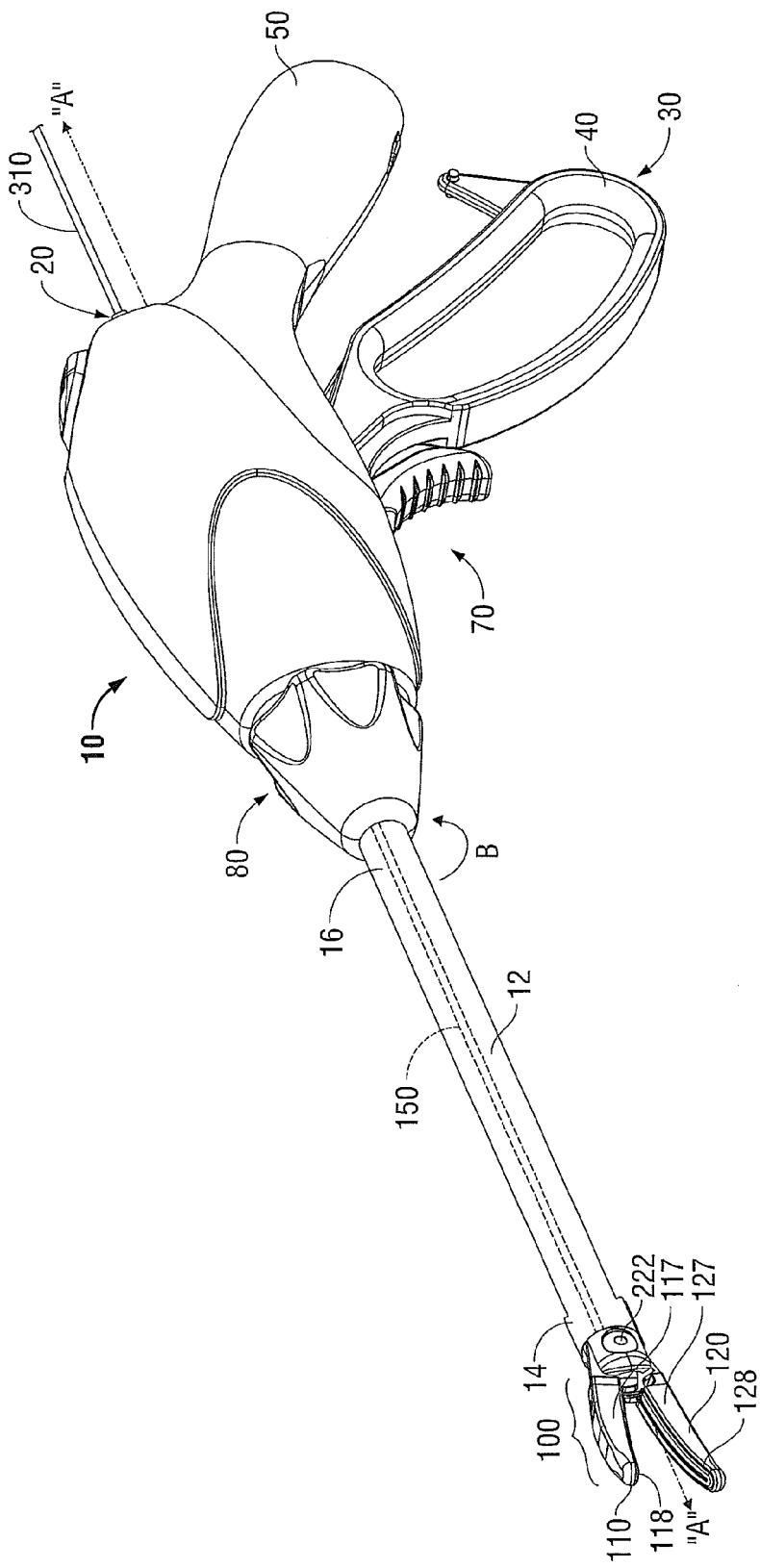
FIG. 1A is a side, perspective view of an endoscopic bipolar forceps showing an end effector assembly including jaw members according to an embodiment of the present disclosure.
Figure 1B:
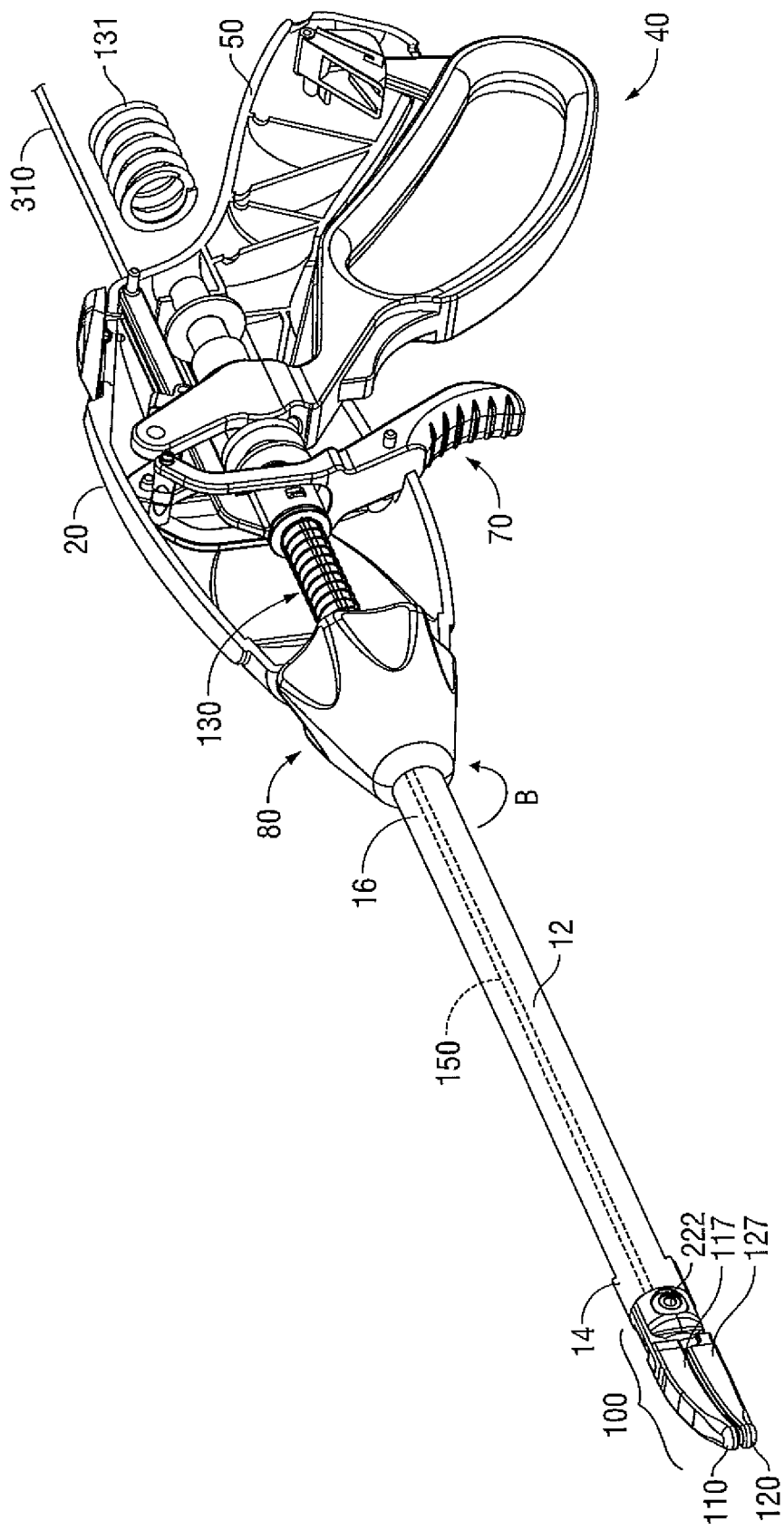
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus, e.g., a bipolar forceps 10 is shown. Bipolar forceps 10 is operatively and selectively coupled to a suitable energy source, such as, for example, an electrosurgical generator (not shown), for performing an electrosurgical procedure. As noted above, an electrosurgical procedure may include sealing, cutting, cauterizing, coagulating, desiccating, and fulgurating tissue all of which may employ RF energy. The generator may be configured for monopolar and/or bipolar modes of operation. The generator may include or is in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., a cable 310) to one or both seal plates 118, 128.

Bipolar forceps 10 is shown configured for use with various electrosurgical procedures and generally includes a housing 20, an electrosurgical cable 310 that connects the forceps 10 to a source of electrosurgical energy (e.g., electrosurgical generator not shown), a handle assembly 30, a rotating assembly 80, a trigger assembly 70, a drive assembly 130 (see FIG. 1B), and an end effector assembly 100 that operatively connects to the drive assembly 130 and includes a drive element 150. The drive assembly 130 may be in operative communication with handle assembly 30 for imparting movement of one or both of a pair of jaw members 110, 120 of end effector assembly 100. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20. End effector assembly 100 includes opposing jaw members 110 and 120 (FIGS. 1A and 1B) that mutually cooperate to grasp, seal and, in some cases, divide large tubular vessels and large vascular tissues.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 that is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to the drive assembly 130, which together mechanically cooperate to impart movement of one or both of the jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Jaw members 110, 120 are operatively and pivotably coupled to each other and located adjacent the distal end 14 of shaft 12. For illustrative purposes, the end effector 100 is shown including a unilateral jaw configuration, i.e., jaw member 110 is movable with respect to jaw member 120 that is non-movable or stationary with respect to jaw member 110. In the illustrated embodiment, the jaw member 110 is movable from a normally open configuration to the clamping configuration when the movable handle is moved proximally, see FIGS. 1A and 1B, respectively. Respective electrically conductive seal plates 118 and 128 are operably supported on and secured to jaw housings 117 and 127 of respective the jaw members 110 and 120, described in greater detail below. For the purposes herein, jaw members 110 and 120 include jaw housings 117 and 127 and sealing plates 118 and 128, respectively. Jaw housings 117 and 128 are configured to support the seal plates 118 and 128, respectively.

For a more detailed description of the bipolar forceps 10 including handle assembly 30 including movable handle 40, rotating assembly 80, trigger assembly 70, drive assembly 130, jaw members 110 and 120 (including coupling methods utilized to pivotably couple the jaw members 110 and 120 to each other) and electrosurgical cable 310 (including line-feed configurations and/or connections), reference is made to commonly owned U.S. Pat. Publication No. 2007/0173814 filed on Nov. 9, 2006.

Figure 2:
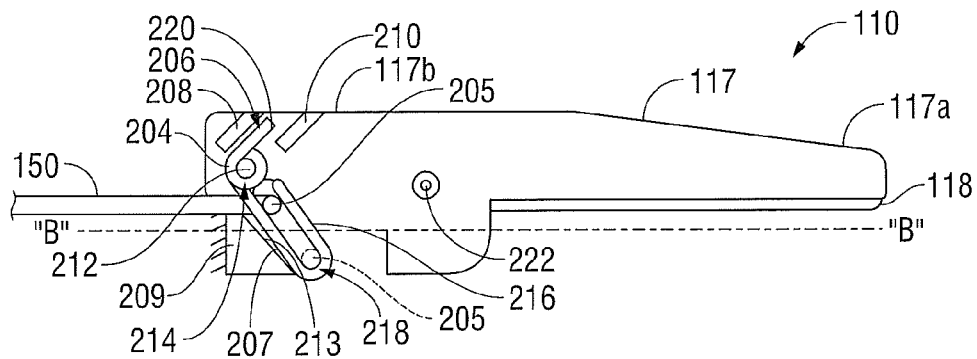
FIG. 2 is a schematic view of a jaw member including a jaw housing depicted in FIGS. 1A and 1B.

Turning now to FIG. 2, one embodiment of jaw housing 117 is shown. It should be noted that, in one embodiment, jaw housings 117 and 127 are substantially identical to each other, and, in view thereof, and so as not to obscure the present disclosure with redundant information, the operative components associated with the jaw housing 117 are described in further detail with respect to jaw member 110, and only those features distinct to housing 127 will be described hereinafter.

With continued reference to FIG. 2, jaw member 110, jaw housing 117, and operative components associated therewith may be formed from any suitable material, including but not limited to metal, metal alloys, plastic, plastic composites, etc. In the embodiment illustrated in FIG. 2, jaw member 110 is formed from metal.

A distal end 117a of the jaw member 110 may be configured to securely engage the electrically conductive seal plate 118 or, with respect to a monolithic jaw member, form the seal plate 118.

A portion of a proximal end 117b of the jaw member 110 is operably secured to the distal end 14 of the shaft 12. More particularly, a portion of proximal end 117b operably couples to the distal end 14 and is in operative communication with a cam member 205 that is operably coupled (via one or more suitable coupling methods, e.g., brazing) to the drive element 150 of the drive assembly 130 such that movement of the drive element 150 causes one or, in some instances, both of the jaw members 110 and 120 to move from the opened position to the closed or clamping position. For example, in one particular embodiment, when the drive element 150 is "pulled," i.e., moved or translated proximally, one or both of the jaw members 110 and 120 is/are caused to move toward the other. Alternatively, and if desired, the drive assembly 130 including the drive element 150 may be configured such that when the drive element 150 is "pushed," i.e., moved or translated distally, one or both of the jaw members 110 and 120 are caused to move toward each other. In certain instances, it may prove useful to have a drive element 150 that is flexible. More particularly, in the illustrated embodiments, where the drive element 150 is operatively associated with an endoscopic instrument (e.g., a bipolar forceps 10 that has a flexible shaft and is configured with jaws associated therewith that are typically quite small, i.e., 3 mm-5 mm), the drive element 150 may be substantially flexible to accommodate bends typically associated with shaft 12 when the bipolar forceps 10 is remotely actuatable relative to the patient.

Proximal end 117b of the jaw member 110 is configured to support one or more resilient members 204. To this end, proximal end 117b of the jaw housing 117 includes a notched area or channel 206 defined by two raised portions 208 and 210. The notched area 206 is configured to securely house a portion of the resilient member 204, described in greater detail below. A raised protrusion or pin 212 of suitable proportion is configured to securely engage the resilient member 204.

Resilient member 204 is operably associated with the housing 117. More particularly, one or more types of resilient members e.g., a resilient member 204, may be utilized to generate a closure force at the jaw members 110 and 120 of the end effector 100 when the jaw members 110 and 120 are in a closed or clamped position. In one embodiment, the resilient member 204 cooperates with the drive assembly 130 to provide a closure force on the jaw members 110 and 120 for sealing tissue, e.g., in the range of about 3 kg/cm$^2$ to about 16 kg/cm$^2$. Resilient member 204 includes an opening 214 (shown engaged with protrusion 212 and as such not explicitly visible) that is defined at a proximal end of the resilient member 204 that securely engages protrusion 212. An elongated portion 216 defining a cam slot 218 extends from the proximal end of the resilient member 204 adjacent the opening 214 and engages cam member 205 that is operably associated with the drive member 150. Specifically, cam slot 218 is configured to receive cam member 205 (see FIG. 2) and is operably formed and/or positioned at the proximal end 117b of the jaw housing 117. More specifically, cam slot 218 includes a generally oblique configuration with respect to a longitudinal axis "B-B" that is parallel to a longitudinal axis "A-A" defined through the shaft 12, see FIGS. 1A and 1B in combination with FIG. 2. Cam slot 218 may extend at an angle that ranges from about 5° to about 30° with respect to the longitudinal axis "B-B." In the embodiment illustrated FIG. 2, cam slot 218 extends at angle that is approximately equal to 45° with respect to the longitudinal axis "B-B." The angle of the cam slot 218 may be selectively varied depending upon a particular instrument, use or manufacturing preference. A proximal end 207 of the cam slot 218 is configured to contact a stop 209 that is operably associated with the shaft 12 and/or end effector 100 such that the jaw member 110 is prevented from rotating past a predetermined point, described in more detail below. A portion of the proximal end of the resilient member 204 is securely housed within the notched area 206 of the jaw housing 117. More particularly, a finger 220 of suitable proportion extends from the proximal end of the resilient member 204 and is securely housed within the notched area 206. The finger 204 is configured to contact one or both of the raised portions 208 and 210 when the jaw member 110 is moved from the open position to the clamping position.

One or more suitable pivot mechanisms may be operably associated with the jaw housing 117 to provide a point of pivot for one or both of the jaw members 110 and 120. For example, a pivot pin 222 may be operably disposed on jaw housing 117 and operably couples to an aperture or opening (not explicitly shown) disposed on the jaw housing 117 (FIG. 2) adjacent the distal end 117a of the jaw housing 117.

One or more type of lubricious materials (not shown), e.g., PTFE, may coat cam slot 218 and/or an internal portion of the elongated portion 216. Coating the cam slot 218 with the lubricious material facilitates movement of the cam member 205 within the cam slot 218 when the drive element is translated proximally (or distally).

Stop 209 is operably disposed adjacent the resilient member 204. Stop 209 functions to provide the proper amount of deflection for the resilient member 204 such that a closure force in the range of about 3 kg/cm$^2$ to about 16 kg/cm$^2$ is present between the jaw members 110 and 120 when the jaw members 110 and 120 are in the clamping position. To this end, stop 209 includes a generally triangular configuration having a sloped or angled distal leading end 213 that is substantially parallel to the elongated portion 216 and cam slot 218 when cam member 205 is positioned at a distal end of the cam slot 218. Stop 209 may be made from any suitable material including but not limited to metal, plastic, etc. In the illustrated embodiment, stop 209 is monolithically formed with the end effector 100 and includes a substantially rigid configuration. In certain embodiments, it may prove useful to make stop 209 relatively resilient. Stop 209 is configured to contact a portion, e.g., proximal end 207 of elongated portion 216, of the resilient member 204 when the cam member 205 is translated a predetermined distance proximally within the cam slot 218. More particularly, when the movable handle 40 moves proximally, the drive element 150 moves proximally, which, in turn, causes the cam member 205 to move proximally from an initial position (shown in phantom in FIG. 2) that corresponds to the jaw member 110 being in the open position, to a subsequent, or final, position that corresponds to the jaw member 110 being in the clamping position (FIG. 2). As the cam member 205 moves from the initial position towards the final position, the elongated portion 216 including the cam slot 218 of the resilient member 204 moves proximally towards the stop 209, which, in turn, causes the resilient member 204 to deflect. Deflection of the resilient member 204 causes the jaw member 110 to move from the open position towards the clamping position. When the elongated portion 216 including the cam slot 218 moves a predetermined distance, the stop 209 and proximal end 207 of the elongated portion 216 are configured to contact each other (FIG. 2). Contact between the stop 209 and proximal end 207 results in the proper amount of deflection for the resilient member 204 and, thus, the necessary closure force needed between the jaw members 110 and 120.

In an assembled configuration each of the jaw members 110 and 120 are positioned in side-by-side relation. As noted above, the cam member 205 is operably coupled to the drive element 150 (or other suitable driving device) and is positioned within the cam slot 218 operably associated with the jaw member 110. Pivot pin 222 is positioned within the opening associated with jaw member 110. As noted above, the pivot pin 222 provides a point of pivot for the jaw member 110. Once assembled, the jaw member 110 and/or jaw member 120 may be pivotably supported at the distal end 14 of the shaft 12 by known methods, such as, for example, by the method described in commonly-owned U.S. Pat. No. 7,597, 693 to Garrison filed on Jun. 13, 2003.

In the instance where the end effector 100 includes a bilateral jaw configuration, each of jaw members 110 and 120 includes a respective resilient member 204 with an elongated portion 216 including a cam slot 218. In this instance, the drive element 150 may be configured to accommodate movement of both of the jaw members 110 and 120. For example, the drive element 150 may include a bifurcated distal end that is configured to operably couple to a respective cam slot 218. In this instance, each of the bifurcated ends may include a respective earn member 205 that operably couples to a respective cam slot 218. It will be appreciated that other configurations of the drive element 150 may be utilized to effect movement of the jaw members 110 and 120 when the jaw members 110 and 120 employed in the bilateral configuration.

Operation of the forceps 10 is now described in terms of use with the end effector 100 illustrated in FIGS. 1A and 1B, i.e., an end effector 100 that utilizes a unilateral jaw configuration.

In use, jaw member 110 is initially in an open position. Tissue is positioned between the jaw members 110 and 120 and, subsequently, movable handle 40 is moved proximally. Proximal movement of movable handle 40 causes the drive element 150 to move proximally. Proximal movement of the drive element 150 causes cam member 205 positioned within the cam slot 218 on jaw housing 117 to move proximally against the bias of the resilient member 204, which, in turn, causes jaw member 110 to move toward jaw member 120, such that tissue is clamped between the jaw members 110 and 120. When the cam member 205 is moved, i.e., "pulled," to a set position, e.g., a position when the jaw members 110 and 120 are in the closed or clamped position and where the proximal end 207 of elongated portion 216 contacts the distal leading end 213 of the stop 209, the biased cam member 205 generates a sealing or closure force at the jaw members 110 and 120. The combination of jaw housing 117 with a resilient member 204 provides a consistent, uniform tissue effect, e.g., tissue seal. Moreover, the combination of jaw housing 117 and resilient member 204 (or other suitable springs, e.g., leaf spring) provides an additional mechanical advantage at the jaws 110 and 120. More particularly, the frictional losses that are associated with a forceps when a drive element is translated within a shaft is offloaded and/or diminished by the resilient member 204 operably associated with the jaw housing 117.

Figure 3:
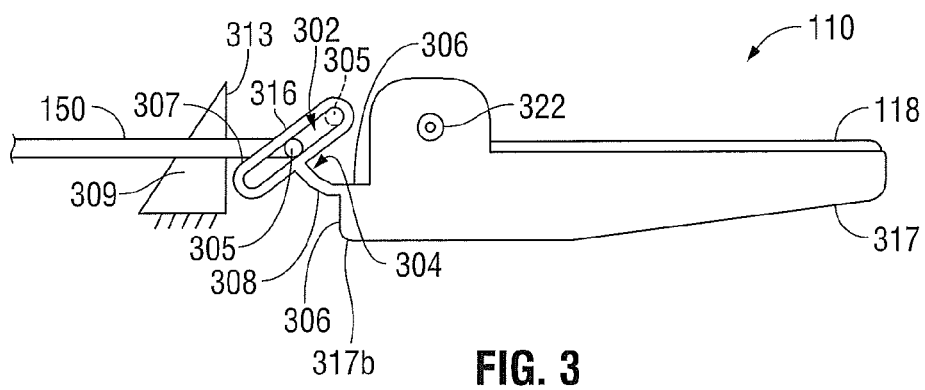
FIG. 3 is a schematic view of a jaw member including a jaw housing according to another embodiment of the present disclosure.

With reference now to FIG. 3, an alternate embodiment of a jaw housing is shown designated jaw housing 317. Jaw housing 317 is similar to jaw housings 117 and so as not to obscure the present disclosure with redundant information, only those operative features and components that are unique to jaw housing 317 are described. For illustrative purposes, jaw housing 317 and operative components associated therewith are described in terms of use with jaw member 110.

In the embodiment illustrated in FIG. 3, one or more types of resilient or spring-like structures are monolithically formed with the jaw housing 317 during the manufacturing process. Monolithically forming the jaw housing 317 with a resilient member(s) decreases the amount of working components, e.g., resilient member 204, needed to provide the closure or sealing forces, e.g., in the range of about 3 kg/cm$^2$ to about 16 kg/cm$^2$ or about 120 pounds per square inch, at the jaw members 110 and 120, which, in turn, reduces the overall cost in the manufacture of the end effector 100 and/or jaw members 110 and 120.

With continued reference to FIG. 3, a resilient member 304 of suitable proportion is operably associated with the jaw housing 317. More particularly, resilient member 304 is monolithically formed, e.g., molded, with the jaw housing 317. Alternatively, resilient member 304 may be a separate component, e.g., coil spring, leaf spring, resilient member 204, etc., that is operably coupled to the jaw housing 317 by any suitable method(s). The amount of flexibility of the resilient member 304 may be dependent on the type of material of the resilient member 304 is made from, the dimensions associated with the resilient member 304, and/or one or more other variables not explicitly described herein. In the illustrated embodiment, resilient member 304 is made from the same material, e.g., metal, as the jaw member 110. Accordingly, the dimension of the resilient member 304 is designed appropriately such that a desired amount of "flex" is obtained when a cam member 305 is translated within an elongated member 316 that defines a generally elongated cam slot 302. Resilient member 304 extends from a bottom wall 306 of a proximal end 317*b* of the jaw housing 317. More particularly, resilient member 304 includes a generally elongated upright portion 308 that extends in a generally orthogonal orientation from bottom wall 306 when the jaw member 110 is in an open position (not explicitly shown). Upright portion 308 of resilient member 304 supports and/or couples to elongated member 316. Cam slot 302 dimensioned to house a cam member 305 and configured to move the jaw member 110. This configuration of an upright portion 308 facilitates flexing or pivoting the elongated cam slot 302 when cam member 305 is moved proximally within the elongated cam slot 302. Cam member 305 is configured and operates similar to other previously described cam members, e.g., cam member 205. More particularly, cam member 305 operably couples to a drive element 150 and is configured to translate within the elongated cam slot 302 when the drive element 150 is translated proximally or, in some instances, distally.

A pivot pin 322 is operably disposed on the jaw housing 317. Pivot pin 322 functions in a manner that is substantially similar to that of pivot pin 222. Accordingly, pivot pin 322 is not described in further detail.

A stop 309 is operably disposed adjacent the elongated cam slot 302 and is configured to function similarly to that of stop 209. More particularly, stop 309 is configured to contact a portion, e.g., a trailing edge or proximal end 307, of elongated cam slot 302 when the cam member 305 is translated proximally within the elongated cam slot 302. A distinguishing feature of the stop 309 when compared to stop 209 is the general shape of the stop 309. More particularly, in the illustrated embodiment, a leading end 313 of the stop 309 is disposed in a generally orthogonal orientation with respect the elongated cam slot 302 as opposed to a parallel orientation as described above with respect to leading end 213 of stop 209 and cam slot 218.

Operation of the jaw housing 317 is substantially similar to that of jaw housing 117. As a result thereof, only those operative features that are unique to jaw housing 317 are described in detail.

In use, proximal movement of the drive element 150 causes cam member 305 positioned within the cam slot 302 on jaw housing 317 to move proximally against the bias of the resilient member 304, which, in turn, causes one or both of the jaw members, e.g., jaw member 110 to move toward the other jaw member, e.g., jaw member 120, such that tissue is clamped between the jaw members 110 and 120. When the cam member 305 is moved, i.e., "pulled," to a set position, e.g., a position when the jaw members 110 and 120 are in the closed or clamped position and when the elongated member 316 contacts the leading end 313 of the stop 309, the biased cam member 305 generates the appropriate closure force at the jaw members 110 and 120.

Figure 4:
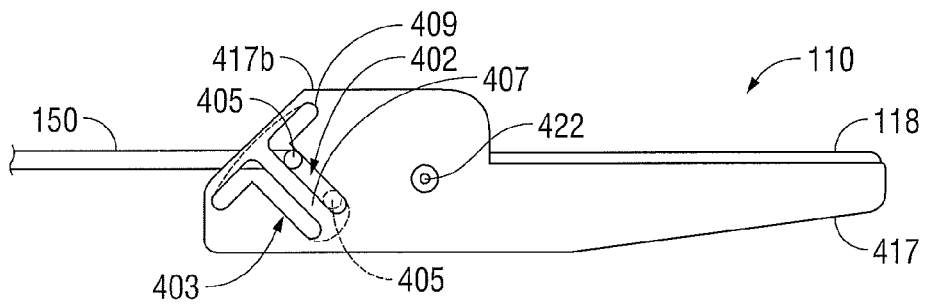
FIG. 4 is a schematic view of a jaw member including jaw housing according to yet another embodiment of the present disclosure.
Figure 5:
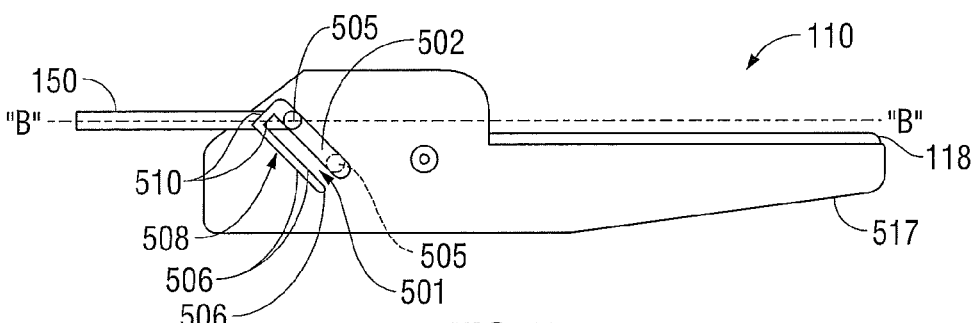
FIG. 5 is a schematic view of a jaw member including jaw housing according to still another embodiment of the present disclosure.

With reference to FIGS. 4 and 5, alternate embodiments of a monolithically formed resilient member that may be utilized with a respective jaw housing 417 and 517 are shown. More particularly, in the embodiments illustrated in FIGS. 4 and 5 each of jaw housing 417 and 517 includes a generally rectangular configuration with one or more cut-outs that serve as a resilient member that provide the closure or sealing forces, e.g., in the range of about 3 kg/cm$^2$ to about 16 kg/cm$^2$, at the jaw members 110 and 120, which, in turn, reduces the overall cost in the manufacture of the end effector 100 and/or jaw members 110 and 120.

With reference now to FIG. 4, jaw housing 417 includes a cam slot 402 that is configured to house a cam member 405. The configuration of cam slot 402 and cam member 405 is similar to that of cam slot 218 and cam member 205. A distinguishing feature of the cam slot 402 when compared the cam slot 218 is that the cam slot 402 includes a generally elongated extension 409 that provides a degree of compliancy to the cam slot 402. A pivot pin 422 couples to the jaw housing 417 and functions in a manner similar to that of the previously described pivot pins, e.g., pivot pin 322.

A slit 403 is operably disposed along a length of a proximal end 417b of the jaw housing 417. Specifically, slit 403 is operably positioned along a length of the jaw housing 417 adjacent the cam slot 402. More specifically, a generally "L" shaped slit 403 is positioned proximally with respect to cam slot 402. In the embodiment illustrated in FIG. 4, an area (indicated by phantom lines) between the slit 403 and cam slot 402 serves as a resilient beam or cushion 407 that provides a degree of flexibility when the cam member 405 is translated proximally within the cam slot 402.

In use, proximal movement of the drive element 150 causes cam member 405 positioned within the cam slot 402 on jaw housing 417 to move proximally against the bias of the cushion 407, which, in turn, causes one or both of the jaw members, e.g., jaw member 110 to move toward the other jaw member, e.g., jaw member 120, such that tissue is clamped between the jaw members 110 and 120. When the cam member 405 is moved, i.e., "pulled," to a set position, e.g., a distal most position within the cam slot 402, the biased cam member 405 generates a closure force at the jaw members 110 and 120.

With reference now to FIG. 5, jaw housing 517 includes a monolithically formed notched area 501 having suitable dimensions. More particularly, notched area 501 creates a cantilever beam spring configuration. More particularly, the cantilever beam spring configuration is defined by notched area 501 that includes three sidewalls 506 that collectively define a generally slanted base section 508 of suitable dimensions. A pair of sidewalls 510 extends from the base section 508. The pair of sidewalls 510 extends orthogonally from the base section 508 and is slanted with respect to the longitudinal axis "B-B." The pair of sidewalls 510 operably couples the base section 508 to a spring arm 501 that forms one side of a cam slot 502. Cam slot 502 is dimensioned to house a cam member 505. In the embodiment illustrated in FIG. 5, cam slot 502 is proportionally larger than the pair of sidewalls 510. More particularly, the pair of sidewalls 510 defines a width (or in some instances may be wider) that is smaller than a width of the cam slot 502. The smaller width of the pair of sidewalls 510 facilitates flexing or pivoting the cam slot 502 when cam member 505 is moved proximally within the cam slot 502.

In use, proximal movement of the drive element 150 causes cam member 505 positioned within the cam slot 502 on jaw housing 517 to move proximally against the bias of the cam slot 502 that serves as a spring arm, which, in turn, causes one or both of the jaw members, e.g., jaw member 110, to move toward the other jaw member, e.g., jaw member 120, such that tissue is clamped between the jaw members 110 and 120. When the cam member 405 is moved, i.e., "pulled," to a set position, e.g., a distal most position within the cam slot 502, the biased cam member 505 generates a closure force at the jaw members 110 and 120.

Figure 6:
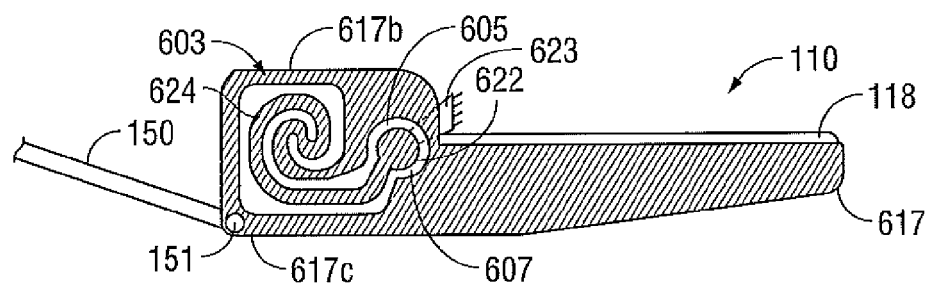
FIG. 6 is a schematic view of a jaw member including jaw housing according to still yet another embodiment of the present disclosure.
Figure 7:
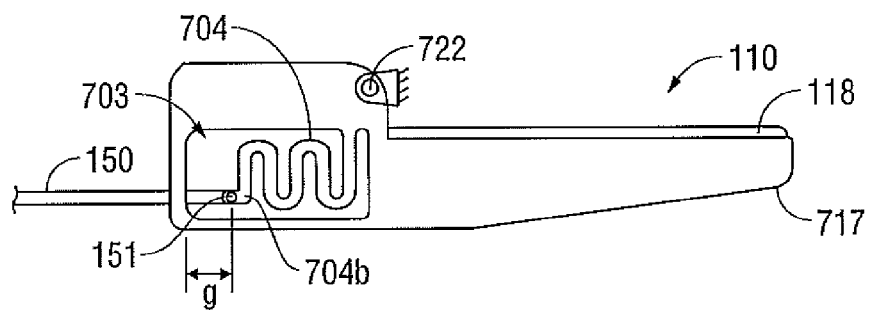
FIG. 7 is a schematic view of a jaw member including jaw housing according to still yet another embodiment of the present disclosure.
Figure 8:
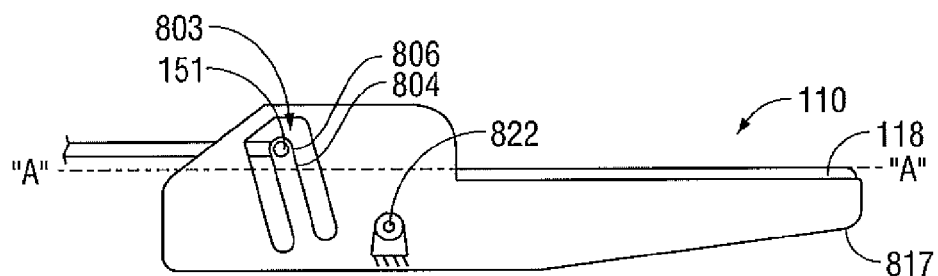
FIG. 8 is a schematic view of a jaw member including jaw housing according to still yet another embodiment of the present disclosure.

With reference to FIGS. 6-8, alternate embodiments of a monolithically formed resilient member that may be utilized with respective jaw housings 617-817 are shown. More particularly, in the embodiments illustrated in FIGS. 6-8 each of jaw housing 617-817 includes a generally rectangular configuration with one or more slits or cut-outs that serve as or house a resilient member that provides the requisite closure or sealing forces, e.g., in the range of about 3 kg/cm$^2$ to about 16 kg/cm$^2$, at the jaw members 110 and 120.

With reference to the FIG. 6, jaw housing 617 includes one or more compression slits or cut-outs 603. In the embodiment illustrated in FIG. 6, jaw housing 617 includes a generally spiral shaped compression slit 603 (slit 603) that is operably disposed along a length of a proximal end 617b of the jaw housing 617. Specifically, slit 603 includes two non-intersecting branches 605 and 607 that meet at a location that is adjacent to pivot 622 that pivotably couples jaw member 110 to the shaft 12. More specifically, each of the branches 605 and 607 wraps around the pivot 622 and extends along a generally spiral path throughout the proximal end 6176 of the jaw housing 617. In the embodiment illustrated in FIG. 6, the slit 603 serves as a resilient member or cushion that provides a degree of flexibility when the drive element 150 is moved proximally. The drive element 150 operably couples to a bottom portion 617c of the proximal end 617b of the jaw housing 617 via one or more coupling methods, e.g., a pin or rivet 151. Pivot 622 is rigidly attached to boss 623 which prevents pivot post 622 from rotating. Rather jaw housing 617 with slots 605 and 607 are allowed to rotate around pivot post 622 while either tensioning or relaxing spring member 624. Spring member 624 may be biased to hold the jaw members 110 and 120 either in the open or closed position when the device is at rest. Boss 623 may be part of shaft 12 or a separate part attached to shaft 12. In the embodiment illustrated in FIG. 6, the slit 603 maintains the jaw member 110 in the clamping position and generates the appropriate closure force at the jaw members 110 and 120.

In use, proximal movement of the drive element 150 causes jaw member 110 to rotate and move away from the jaw member 120 such that tissue may be positioned therebetween. Thereafter, movable handle 40 is released which, in turn, causes the drive element 150 to move distally and the jaw member 110 to move back to the clamping position such that tissue is clamped between the jaw members 110 and 120. When the jaw members 110 and 120 are in the clamping position, the slit 603 is configured to generate the appropriate closure force, e.g., in the range of about 3 kg/cm$^2$ to about 16 kg/cm$^2$, between the jaw members 110 and 120.

With reference to the FIG. 7, jaw housing 717 includes a cavity 703. Cavity 703 is configured to house one or more types of resilient members 704. In the embodiment illustrated in FIG. 7, the resilient member 704 is a monolithically formed resilient member in the form of a compression spring 704. The compression spring 704 is configured to expand and contract within the confines of the cavity 703. The compression spring 704 is disposed below a pivot pin 722 to facilitate rotating the jaw member 110. The drive element 150 operably couples to a proximal end 704b of compression spring 704 by one or more suitable coupling methods, e.g., a rivet or pin 151. In the embodiment illustrated in FIG. 7, the compression spring 704 does not bias the jaw member 110 in either the open position or closed position. Rather, compression spring 704 serves to regulate the clamping force of jaw member 110 when drive member 150 is moved distally or proximally.

In the embodiment illustrated in FIG. 7, the drive member 150 biases the jaw member 110 closed when moved distally and open when moved proximally. The at rest gap "g" may be adjusted to achieve a desired opening and closing force regulation.

Optionally, compression spring 704 may be formed from the base jaw material of jaw member 110 as shown, or it may be inserted as a separate part made from other suitable material. As such, a separate compression spring 704 may be longer than cavity 703 in its free state and it could be compressed upon assembly into opening 703 to provide a desired amount of preload in the spring to help achieve a desired clamping force characteristic.

In use, jaw member 110 is initially in the open position. Tissue is positioned between the jaw members 110 and 120. Proximal movement of the movable handle 40 causes distal movement of the drive element 150, which, in turn, causes jaw member 110 to rotate and move about the pivot 222 and toward the jaw member 120 such that tissue may be clamped therebetween. When the jaw members 110 and 120 are in the clamping position, the compression spring 704 is configured to generate the appropriate closure force, e.g., in the range of about 3 kg/cm² to about 16 kg/cm², between the jaw members 110 and 120.

With reference to the FIG. 8, jaw housing 817 includes a cut-out 803. Cut-out 803 is configured to house one or more types of resilient members 804. In the embodiment illustrated in FIG. 8, the resilient member 804 is a monolithically formed resilient member in the form of a cantilever spring 804 of suitable dimensions. The cantilever spring 804 includes a generally elongated configuration and is disposed in an angled or oblique relation with respect to the longitudinal axis "A-A." The angle at which the cantilever spring 804 is oriented ranges from about 0 to about 180°. In the embodiment illustrated in FIG. 8, cantilever spring 804 is oriented at an angle that ranges from about 45° to about 90°. Cantilever spring 804 includes a top portion 806 that operably couples to the drive element 150 by one or more suitable coupling methods, e.g., rivet or pin 151. The cantilever spring 804 is disposed above a pivot pin 822 to facilitate rotating the jaw member 110. In the embodiment illustrated in FIG. 8, the cantilever spring 804 does not maintain the jaw member 110 in either the open position or the closed position.

In use, jaw member 110 is initially in the open position. Tissue is positioned between the jaw members 110 and 120. Proximal movement of the movable handle 40 causes proximal movement of the drive element 150, which, loads spring 804, which, in turn, causes jaw member 110 to rotate and move about the pivot pin 822 and toward the jaw member 120 such that tissue may be clamped therebetween. When the jaw members 110 and 120 are in the clamping position, the cantilever spring 804 is configured to generate the appropriate closure force, e.g., in the range of about 3 kg/cm² to about 16 kg/cm², between the jaw members 110 and 120.

Figure 9:
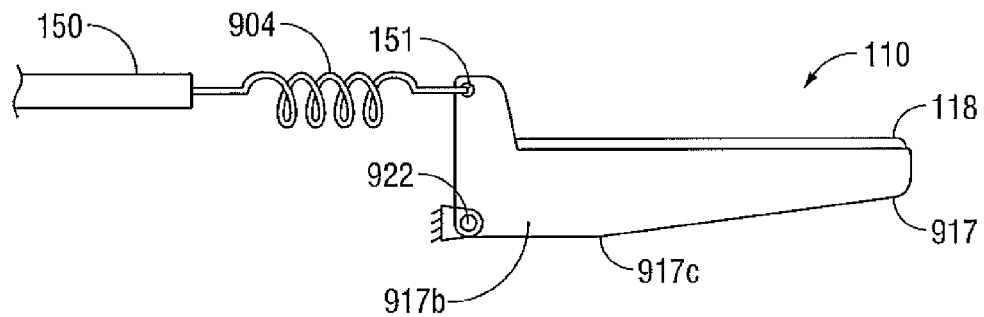
FIG. 9 is a schematic view of a jaw member including jaw housing according to still yet another embodiment of the present disclosure.

With reference now to FIG. 9, an alternate embodiment of a jaw housing is shown designated jaw housing 917. Jaw housing 917 is similar to the previously described jaw housings, e.g., jaw housing 117, and so as not to obscure the present disclosure with redundant information, only those operative features and components that are unique to jaw housing 917 are described.

Jaw housing 917 includes a proximal end 917b that operably couples to a distal end of a resilient member (e.g., in the form of a tension spring 904) by one or more of the previously described coupling methods, e.g., rivets or, pin 151. A proximal end of the tension spring 904 operably couples to the drive element 150 by one or more of the previously described coupling methods, e.g., brazing. Unlike the previously described jaw housings, e.g., jaw housing 117, a bottom portion 917c of the jaw housing 917 operably couples to a pivot pin 922 that is fixedly coupled to an internal frame of the shaft 12. Coupling the jaw housing 917 in this manner facilitates rotating the jaw member 110 when the drive element 150 is pulled proximally.

In use, jaw member 110 is initially in the open position. Tissue is positioned between the jaw members 110 and 120. Proximal movement of the movable handle 40 causes proximal movement of the drive element 150, which, in turn, causes jaw member 110 to rotate and move about the pivot pin 922 and toward the jaw member 120 against the bias of the tension spring 904 such that tissue may be clamped therebetween. When the jaw members 110 and 120 are in the clamping position, the tension spring 904 is configured to generate the appropriate closure force, e.g., in the range of about 3 kg/cm² to about 16 kg/cm², between the jaw members 110 and 120.

Figure 10:
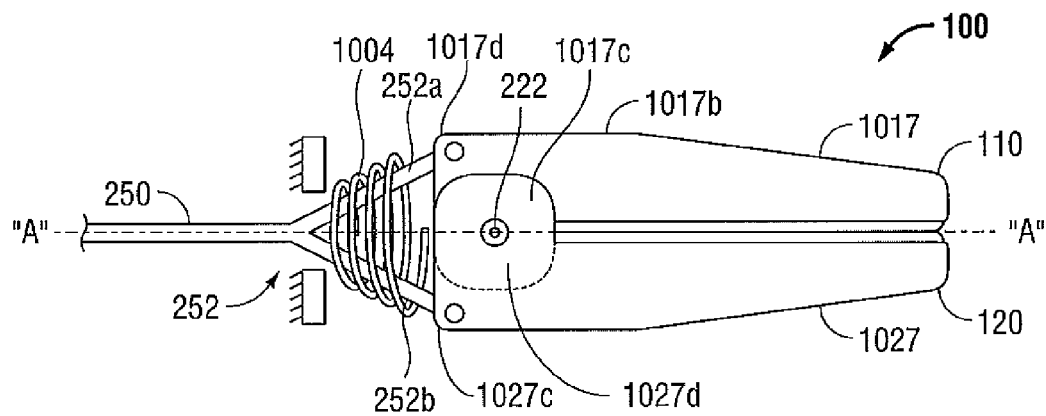
FIG. 10 is a schematic view of jaw members including respective jaw housings according to still yet another embodiment of the present disclosure.
Figure 11:
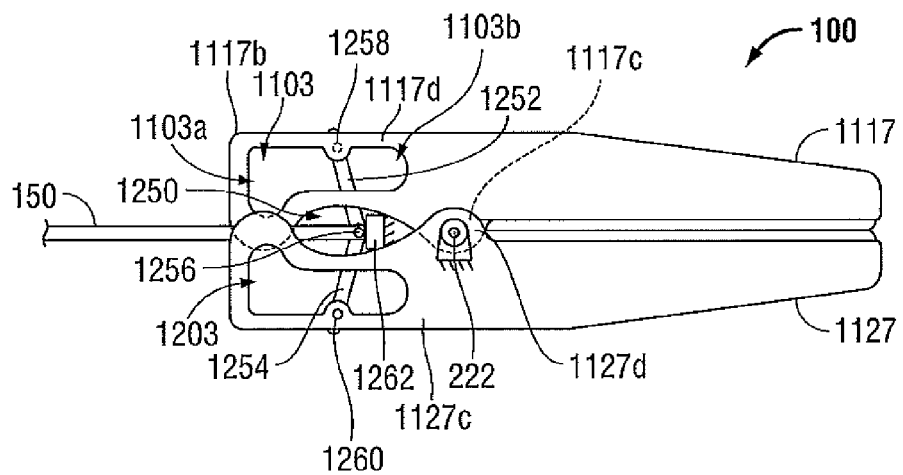
FIG. 11 is a schematic view of jaw members including respective jaw housings according to still yet another embodiment of the present disclosure.

With reference now to FIGS. 10 and 11, an end effector 100 that utilizes a bilateral jaw configuration is shown. That is, both of the jaws 110 and 120 move with respect to each other.

FIG. 10 illustrates an end effector 100 that includes jaw housings 1017 and 1027 that are respectively associated with jaw members 110 and 120. It should be noted that, in one embodiment, jaw housings 1017 and 1027 are substantially identical to each other, and, in view thereof, and so as not to obscure the present disclosure with redundant information, the operative components associated with the jaw housing 1017 are described in further detail with respect to jaw member 110, and only those features distinct to housing 1027 will be described hereinafter.

A proximal end 1017b of the jaw housing 1017 operably couples to a drive element 250. A bottom portion 1017c of the jaw housing 1017 pivotably couples, via a pivot pin, e.g., a pivot pin 222, to a corresponding top portion 1027d of the jaw housing 1027. A top portion 1017d of the jaw housing 1027 is operably coupled to a drive wire 250 (or portion associated therewith) by one or more suitable coupling methods previously described, e.g., brazing. Likewise, a bottom portion 1027c of the jaw housing 1027 is operably coupled to a drive element 250 (or portion associated therewith) by one or more suitable coupling methods previously described, e.g., brazing.

Unlike drive element 150, drive element 250 includes a bifurcated distal end 252 that includes two end portions 252a and 252b that are pivotably coupled to the drive element 250 and respective jaw housings 1017 and 1027. End portions 252a and 252b are oriented in an angled or oblique relation with respect to each other and the longitudinal axis "A-A." End portions 252a and 252b are configured to pivot from an initially spaced-apart position that corresponds to the jaw members 110 and 120 being in the clamping position (FIG. 10), to a subsequent or final position that corresponds to the jaw members 110 and 120 being in the open position (not shown).

One or more resilient members are operably associated with the jaw members 110 and 120. More particularly, a resilient member in the form of a compression spring 1004 is operably coupled to the end portions 252a and 252b via one or more suitable coupling methods. The compression spring 1004 is configured to expand and contract when the end portions 252a and 252b move from the initial to the subsequent or final position.

In use, jaw members 110 and 120 are initially in the clamping position under the bias of the compression spring 1004. When the jaw members 110 and 120 are in the clamping position, the compression spring 1004 is configured to generate the appropriate closure force, e.g., in the range of about 3 kg/cm² to about 16 kg/cm², between the jaw members 110 and 120. Proximal movement of the movable handle 40 causes proximal movement of the drive element 250, which, in turn, causes the end portions 252a and 252b to move from the initial position towards the final position, which, in turn, causes the jaw members 110 and 120 to rotate and move about the pivot pin 222 and move away from one another. Thereafter, tissue is positioned between the jaw members 110 and 120. Subsequently, movable handle is released and the jaw members 110 and 120 move back to the clamping position.

FIG. 11 illustrates an end effector 100 that includes jaw housings 1117 and 1127 that are respectively associated with jaw members 110 and 120. It should be noted that, in one embodiment, jaw housings 1117 and 1127 are substantially identical to each other, and, in view thereof, and so as not to obscure the present disclosure with redundant information, the operative components associated with the jaw housing 1117 are described in further detail with respect to jaw member 110, and only those features distinct to housing 1127 will be described hereinafter.

Similarly to that of bottom portion 1017c of jaw housing 1017, a bottom portion 1117c of jaw housing 1117 is pivotably coupled to a corresponding top portion 1127d of jaw housing 1127. However, unlike jaw housing 1017, jaw housing 1117 includes a top portion 1117d that is operably coupled to a link assembly 1250, described in greater detail below.

A proximal end 1117b of jaw housing 1117 is substantially resilient. More particularly, a notched out area 1103 of suitable dimensions allows the proximal end 1117b to "flex" or give when a drive element 150 is moved distally and the jaw members 110 and 120 move toward the clamping position. In the embodiment illustrated in FIG. 11, the notched out area 1103 includes a generally widened proximal end 1103a and a tapered or narrowed distal end 1103b. This configuration of a widened proximal end 1103a and a tapered or narrowed distal end 1103b facilitates flexing the proximal end 1117b of the jaw housing 1117.

Jaw housing 1127 includes a similar notched out area 1203 of suitable dimensions that functions similarly to that of the notched out area 1103 associated with jaw housing 1117.

Drive element 150 operably couples to the jaw housings 1117 and 1127 via the link assembly 1250. In the illustrated embodiment, drive element 150 operably couples to the link assembly via one or more suitable coupling methods, e.g., a rivet or pin 1256. Drive element 150 is configured such that proximal movement of the movable handle 40 causes the drive element 150 to translate distally, which, in turn, causes the jaw members 110 and 120 to move from an open or neutral position to a clamping position.

Link assembly 1250 includes upper and lower links 1252 and 1254. Links 1252 and 1254 include a generally elongated configuration. Links 1252 and 1254 pivotably couple to each other via pivot pin 1256. Likewise, links 1252 and 1254 are pivotably coupled to a respective upper portion 1117d and lower portion 1127c via respective pivot pins 1258 and 1260. Links 1252 and 1254 are configured to pivot about pivot pins 1256, 1258 and 1260 when the drive element 150 is move distally. The links 1252 and 1254 are configured to pivot from an initial or proximal position, wherein the links are slanted or oblique with respect to the longitudinal axis "A-A," through a transition or center point, wherein the links 1252 and 1254 are in a substantially upright or perpendicular position with respect to the longitudinal axis "A-A," to a final or distal position where the links 1252 and 1254 are again slanted or oblique with respect to the longitudinal axis "A-A" (FIG. 11).

A stop 1262 functions to provide the proper amount of movement of the links 1252, 1254 and drive element 150 when the drive element 150 is moved distally such that a closure force in the range of about 3 kg/cm$^2$ to about 16 kg/cm$^2$ is present between the jaw members 110 and 120 when the jaw members 110 and 120 are in the clamping position. In the illustrated embodiment, stop 1262 includes a generally rectangular configuration. Stop 1262 may be made from any suitable material including but not limited to metal, plastic, etc. In the illustrated embodiment, stop 1262 is monolithically formed with the end effector 100 and includes a substantially rigid configuration. In certain embodiments, it may prove useful to make stop 1262 relatively resilient. Stop 1262 is configured to contact one of the links 1252 and 1254 and/or drive element 150 when the drive element 150 is translated a predetermined distance distally within the shaft 12. More particularly, when the movable handle 40 moves proximally, the drive element 150 moves distally, which, in turn, causes links 1252 and 1254 pivot about respective pivot pins 1258 and 1260 and pivot pin 1256, from an initial position that corresponds to the jaw members 110 and 120 being in the open position, to a subsequent, or final, position that corresponds to the jaw members 110 and 120 being in the clamping position (FIG. 11). When the drive element 150 including links 1252 and 1254 moves a predetermined distance, the stop 1262 and one of the links 1252, 1254 and/or drive element 150 are configured to contact each other (FIG. 11). Contact between the stop 1262 and one of the links 1252, 1254 and/or drive element 150 results in the proper amount of deflection for the proximal ends 1117b and 1127b and, thus, the necessary closure force needed between the jaw members 110 and 120. Stop 1262 prevents and/or impedes further movement of the drive element 150 and the links 1252 and 1254, which, in turn, maintains the jaw members 110 and 120 in the clamping position.

In use, jaw members 110 and 120 are initially in the open or neutral position. Tissue is positioned between the jaw members 110 and 120. Proximal movement of the movable handle 40 causes distal movement of the drive element 150, which, in turn, causes the links 1252 and 1254 to move from the initial position through the center position and towards the final position, which, in turn, causes the jaw members 110 and 120 to rotate and move about the pivot pin 222 and move toward each other. With the links 1252 and 1254 in this position, i.e., past the center line of pins 1258 and 1260, the jaw member 110 and 120 will remain in the clamped position in the absence of force on drive element 250, until, subsequently, movable handle 40 is moved distally to release the jaw members 110 and 120 and move them back to the open or neutral position.

From the foregoing and with reference to the various figure drawings, those skilled in the art will appreciate that certain modifications can also be made to the present disclosure without departing from the scope of the same. For example, other spring mechanisms such as, for example, compressed gas, resilient bladder, spring washers, bellows and compressed air and so forth, may be operably associated with any of the aforementioned configurations of jaw housings, e.g., jaw housing 117, and utilized to generate a closure or sealing force at the jaw members.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
a housing having at least one shaft that extends therefrom that defines a longitudinal axis therethrough;
an end effector assembly operatively connected to a distal end of the at least one shaft including a pair of first and second jaw members, at least one of the first and second jaw members being movable relative to other jaw member from an open position wherein the first and second jaw members are disposed in spaced relation relative to one another, to a clamping position wherein the first and second jaw members cooperate to grasp tissue therebetween; and
a resilient member operably coupled to the at least one movable jaw member, the resilient member defining at least one cam slot operably associated with the at least one movable jaw member, the at least one cam slot configured to receive a cam member such that upon movement thereof rotates the at least one movable jaw member from the open position to the clamping position, the resilient member including a finger extending from a proximal end thereof and housed within a notched area defined by the at least one movable jaw, the resilient member configured to provide a force to bias the jaw members in the clamping position.

2. An endoscopic forceps according to claim 1, wherein the cam slot is disposed at an angle relative to the longitudinal axis.

3. An endoscopic forceps according to claim 1, wherein the resilient member provides a closure force of about 3 kg/cm$^2$ to about 16 kg/cm$^2$.

4. An endoscopic forceps according to claim 1, wherein a stop operably communicates with the at least one movable jaw member and whereupon actuation of the forceps at least partially contacts the at least one of the cam slot when the cam member is actuated.

5. An endoscopic forceps according to claim 1, further including a drive assembly operably associated with the housing and operably coupled to the cam member such that proximal movement of a drive element associated with the drive assembly causes the cam member to translate proximally within the cam slot.

6. An endoscopic forceps according to claim 1, wherein the drive element is flexible.

7. An end effector adapted for use with a forceps including at least one shaft, comprising:
a pair of first and second jaw members, at least one of the first and second jaw members being movable relative to other jaw member from an open position wherein the first and second jaw members are disposed in spaced relation relative to one another, to a clamping position wherein the first and second jaw members cooperate to grasp tissue therebetween;
a resilient member operably coupled to the at least one movable jaw member, the resilient member defining at least one cam slot operably associated with the at least one movable jaw member, the at least one cam slot configured to receive a cam member such that upon movement thereof rotates the at least one movable jaw member from the open position to the clamping position, the resilient member including a finger extending from a proximal end thereof and housed within a notched area defined by the at least one movable jaw, the resilient member configured to provide a force to bias the jaw members in the clamping position.

8. An end effector according to claim 7, wherein the cam slot is disposed at an angle relative to the longitudinal axis.

9. An end effector according to claim 7, wherein the at least one cam slot is defined by the resilient member.

10. An end effector according to claim 7, wherein the resilient member provides a closure force of about 3 kg/cm$^2$ to about 16 kg/cm$^2$.

11. An end effector according to claim 7, wherein a stop operably communicates with the at least one movable jaw member and whereupon actuation of the forceps at least partially contacts the at least one of the cam slot when the cam member is actuated.

12. An end effector according to claim 7, further including a drive assembly operably associated with the housing and operably coupled to the cam member such that proximal movement of a drive rod associated with the drive assembly causes the cam member to translate proximally within the cam slot.

13. An end effector according to claim 7, wherein the drive rod is flexible.

* * * * *